US010562932B2

(12) United States Patent
Tsao et al.

(10) Patent No.: US 10,562,932 B2
(45) Date of Patent: Feb. 18, 2020

(54) SHORT SYNTHETIC PEPTIDE AND USES THEREOF

(71) Applicants: Yeou-Ping Tsao, Taipei (TW); Tsung-Chuan Ho, Taipei (TW)

(72) Inventors: Yeou-Ping Tsao, Taipei (TW); Tsung-Chuan Ho, Taipei (TW)

(73) Assignee: MACKAY MEMORIAL HOSPITAL, Taipei (TW)

(*) Notice: Subject to any disclaimer, the term of this patent is extended or adjusted under 35 U.S.C. 154(b) by 0 days.

(21) Appl. No.: 15/775,835

(22) PCT Filed: Dec. 12, 2016

(86) PCT No.: PCT/CN2016/109504
§ 371 (c)(1),
(2) Date: May 13, 2018

(87) PCT Pub. No.: WO2017/101748
PCT Pub. Date: Jun. 22, 2017

(65) Prior Publication Data
US 2018/0354990 A1    Dec. 13, 2018

Related U.S. Application Data

(60) Provisional application No. 62/267,269, filed on Dec. 14, 2015.

(51) Int. Cl.
*A61K 38/08* (2019.01)
*A61K 38/00* (2006.01)
*C07K 7/06* (2006.01)
*C07K 7/08* (2006.01)
*A61Q 19/00* (2006.01)
*A61P 27/04* (2006.01)
*A61P 17/00* (2006.01)
*A61P 35/00* (2006.01)

(52) U.S. Cl.
CPC .............. *C07K 7/06* (2013.01); *A61P 17/00* (2018.01); *A61P 27/04* (2018.01); *A61P 35/00* (2018.01)

(58) Field of Classification Search
CPC .......... A61K 38/00; A61K 38/08; C07K 7/06; C07K 7/08; A61P 17/00; A61P 27/04; A61P 35/00; A61Q 19/00

USPC ...... 530/328, 300; 514/1.1, 21.6, 20.8, 18.6, 514/18.7, 18.8
See application file for complete search history.

(56) References Cited

U.S. PATENT DOCUMENTS

| | | | | | |
|---|---|---|---|---|---|
| 4,966,848 | A | * | 10/1990 | Smith | C12N 9/1029 435/193 |
| 5,223,421 | A | * | 6/1993 | Smith | C12N 9/1029 435/193 |
| 5,837,218 | A | * | 11/1998 | Peers | A61K 51/088 424/1.69 |
| 2012/0135518 | A1 | * | 5/2012 | Kiessling | C12N 5/0068 435/366 |

FOREIGN PATENT DOCUMENTS

WO    2009114539    9/2009

OTHER PUBLICATIONS

Okazaki et al., "Effect of KAFDITYVRLK (C-16), a Laminin Gamma 1 Chain Peptide, to Tumor Cell Adhesion and Metastasis," Peptide Science, 1999, 201-204.*
Kuratomi et al., "Laminin γ1 chain peptide, C-16 (KAFDITYVRLKF), promotes migration, MMP-9 secretion, and pulmonary metastasis of B16-F10 mouse melanoma cells", Br. J. Cancer, 2002, 86(7), pp. 1169-1173.
Nomizu et al., "Identification of Cell Binding Sequences in Mouse Laminin g1 Chain by Systematic Peptide Screening", J. Biol. Chem., 1997, 272(51), pp. 32198-32205.
Okazaki et al., "Effect of KAFDITYVRLK(C-16), a Laminin Gamma 1 Chain Peptide, to Tumor Cell Adhesion and Metastasis", Peptide Science 1999, 2000, pp. 201-204.
Malinda et al., "Angiogenic Laminin-Derived Peptides Stimulate Wound Healing", Int. J. Biochem. Cell Biol., 2008, 40(12), pp. 2771-2780.

* cited by examiner

*Primary Examiner* — Julie Ha

(57) ABSTRACT

Disclosed herein are synthetic peptides and compositions comprising the same for the treatment and/or prophylaxis of a disease or a condition related to dry eye syndrome, psoriasis vulgaris or multiple myeloma. Also disclosed herein are methods of treating and/or preventing a disease or a condition related to dry eye syndrome, psoriasis vulgaris or multiple myeloma, by administering to a subject in need of such treatment a composition containing a therapeutically effective amount of a synthetic peptide of the present disclosure.

6 Claims, 9 Drawing Sheets
Specification includes a Sequence Listing.

A

B

SEQUENCE LISTING

```
<160> NUMBER OF SEQ ID NOS: 13

<210> SEQ ID NO 1
<211> LENGTH: 9
<212> TYPE: PRT
<213> ORGANISM: Artificial Sequence
<220> FEATURE:
<223> OTHER INFORMATION: synthetic
<220> FEATURE:
<221> NAME/KEY: VARIANT
<222> LOCATION: 1
<223> OTHER INFORMATION: Xaa is any amino acid residue
<220> FEATURE:
```

```
<221> NAME/KEY: VARIANT
<222> LOCATION: 5
<223> OTHER INFORMATION: Xaa is any amino acid residue
<220> FEATURE:
<221> NAME/KEY: VARIANT
<222> LOCATION: 9
<223> OTHER INFORMATION: Xaa is any amino acid residue

<400> SEQUENCE: 1

Xaa Ile Thr Tyr Xaa Arg Leu Lys Xaa
1               5

<210> SEQ ID NO 2
<211> LENGTH: 9
<212> TYPE: PRT
<213> ORGANISM: Artificial Sequence
<220> FEATURE:
<223> OTHER INFORMATION: synthetic; 9-mer

<400> SEQUENCE: 2

Asp Ile Thr Tyr Val Arg Leu Lys Phe
1               5

<210> SEQ ID NO 3
<211> LENGTH: 9
<212> TYPE: PRT
<213> ORGANISM: Artificial Sequence
<220> FEATURE:
<223> OTHER INFORMATION: synthetic; 9-mer Da

<400> SEQUENCE: 3

Ala Ile Thr Tyr Val Arg Leu Lys Phe
1               5

<210> SEQ ID NO 4
<211> LENGTH: 9
<212> TYPE: PRT
<213> ORGANISM: Artificial Sequence
<220> FEATURE:
<223> OTHER INFORMATION: synthetic; 9-mer Ia

<400> SEQUENCE: 4

Asp Ala Thr Tyr Val Arg Leu Lys Phe
1               5

<210> SEQ ID NO 5
<211> LENGTH: 9
<212> TYPE: PRT
<213> ORGANISM: Artificial Sequence
<220> FEATURE:
<223> OTHER INFORMATION: synthetic; 9-mer Ta

<400> SEQUENCE: 5

Asp Ile Ala Tyr Val Arg Leu Lys Phe
1               5

<210> SEQ ID NO 6
<211> LENGTH: 9
<212> TYPE: PRT
<213> ORGANISM: Artificial Sequence
<220> FEATURE:
<223> OTHER INFORMATION: synthetic; 9-mer Ya

<400> SEQUENCE: 6

Asp Ile Thr Ala Val Arg Leu Lys Phe
1               5
```

```
<210> SEQ ID NO 7
<211> LENGTH: 9
<212> TYPE: PRT
<213> ORGANISM: Artificial Sequence
<220> FEATURE:
<223> OTHER INFORMATION: synthetic; 9-mer Va

<400> SEQUENCE: 7

Asp Ile Thr Tyr Ala Arg Leu Lys Phe
1               5

<210> SEQ ID NO 8
<211> LENGTH: 9
<212> TYPE: PRT
<213> ORGANISM: Artificial Sequence
<220> FEATURE:
<223> OTHER INFORMATION: synthetic; 9-mer Ra

<400> SEQUENCE: 8

Asp Ile Thr Tyr Val Ala Leu Lys Phe
1               5

<210> SEQ ID NO 9
<211> LENGTH: 9
<212> TYPE: PRT
<213> ORGANISM: Artificial Sequence
<220> FEATURE:
<223> OTHER INFORMATION: synthetic; 9-mer La

<400> SEQUENCE: 9

Asp Ile Thr Tyr Val Arg Ala Lys Phe
1               5

<210> SEQ ID NO 10
<211> LENGTH: 9
<212> TYPE: PRT
<213> ORGANISM: Artificial Sequence
<220> FEATURE:
<223> OTHER INFORMATION: synthetic; 9-mer Ka

<400> SEQUENCE: 10

Asp Ile Thr Tyr Val Arg Leu Ala Phe
1               5

<210> SEQ ID NO 11
<211> LENGTH: 9
<212> TYPE: PRT
<213> ORGANISM: Artificial Sequence
<220> FEATURE:
<223> OTHER INFORMATION: synthetic; 9-mer Fa

<400> SEQUENCE: 11

Asp Ile Thr Tyr Val Arg Leu Lys Ala
1               5

<210> SEQ ID NO 12
<211> LENGTH: 12
<212> TYPE: PRT
<213> ORGANISM: Artificial Sequence
<220> FEATURE:
<223> OTHER INFORMATION: synthetic; 12-mer

<400> SEQUENCE: 12

Lys Ala Phe Asp Ile Thr Tyr Val Arg Leu Lys Phe
1               5                   10

<210> SEQ ID NO 13
```

```
<211> LENGTH: 8
<212> TYPE: PRT
<213> ORGANISM: Artificial Sequence
<220> FEATURE:
<223> OTHER INFORMATION: synthetic; 8-mer

<400> SEQUENCE: 13

Ile Thr Tyr Val Arg Leu Lys Ala
1               5
```

SHORT SYNTHETIC PEPTIDE AND USES THEREOF

CROSS-REFERENCE TO RELATED APPLICATIONS

This application is a national stage of PCT international Application No. PCT/CN2016/109504, filed on Dec. 12, 2016 and published in English on Jun. 22, 2017 with the Publication No. WO 2017/101748A1, and claims priority to U.S. Provisional Patent Application No. 62/267,269, filed Dec. 14, 2015, which is incorporated herein by reference in its entirety.

BACKGROUND OF THE INVENTION

1. Field of the Invention

The present disclosure relates to the discovery of a short synthetic peptide, and its use for the treatment and/or prophylaxis of diseases and/or conditions related to dry eye syndrome, psoriasis vulgaris or multiple myeloma.

2. Description of Related Art

Dry eye syndrome, commonly referred to as "dry eyes," is a prevalent eye condition resulting generally from any abnormality in the tear production process, such as decreased tear production, excessive tear evaporation, or an abnormality in mucin or lipid component of the tear film that covers the normal ocular surface. The typical symptoms of the dry eye syndrome include dryness, grittiness, irritation, difficulty reading for long periods of time, burning, and even the apparent contradiction of excessive tearing or watering. In extreme cases, patients may become unusually sensitive to light, experience severe pain in the eyes, and start to notice diminished vision. The conventional treatment for dry eyes involves treating the symptoms rather than the cause. For example, artificial tears and ocular lubricants are a common treatment. Although artificial tears may provide temporary relief, they merely palliate the symptoms. Furthermore, the preservatives used in the artificial tears can actually aggravate the condition, and can even kill corneal cells. Thus far, there have been few approaches to the treatment of dry eye disorders that are effective in addressing all the issues regarding dry eye syndrome.

Psoriasis is characterized by pink or red lesions which are covered with silvery scales. These lesions are often found in the folds of the elbows and knees, the scalp, and the genitoanal area. The condition is marked by accelerated turnover of the epidermal layer of the skin and consequential epidermal thickness. While normal epidermal turnover occurs every 25-30 days, in psoriatic skin it occurs approximately every 3-4 days. At this rate, the skin color is often affected, resulting in too much or too little pigmentation. The duration of psoriasis vulgaris is variable. Psoriatic lesions may last a lifetime, or they may disappear within a short period of time. Many attempts have been made in the past to cure psoriasis vulgaris. The first attempts to treat this condition were through topical agents containing salicylic acid as the active ingredient. However, because salicylic acid is an irritant, its use sometimes resulted in worsening the condition. Another popular active ingredient of the topical agents is corticosteriod such as hydrocortisone. The corticosteriod may significantly suppress psoriasis. However, they also generate many side effects, such as local atrophy and systemic absorption. There is also a danger of relapse upon discontinuance of use. In a different approach, exposure to ultraviolet light has been tried, but has met with limited success. Combination therapy of ultraviolet light and coal tar preparations appear to be more effective than the ultraviolet light alone. However, some patients incur a worsening of their condition upon the application of coal tar to affected areas. Other systemic treatments which have been tried include cytostatic therapy and Vitamin A and C treatments; however, the value of such treatment remains questionable. Thus far, none of the treatments for psoriasis vulgaris have been successful, they are either ineffective or accompanied by undesired side effects.

Multiple myeloma represents a malignant proliferation of plasma cells derived from a single clone. Despite recent advances in the development of new classes of anti-cancer drugs for the treatment of multiple myeloma, no curative therapy currently exists for this disease, which is the $2^{nd}$ most commonly diagnosed hematologic malignancy in the Western World. Therefore, the identification of new therapeutic agents with anti-multiple myeloma activity remains an urgent priority.

Accordingly, there exists a need in the related filed an improved medication and/or method for treating and/or preventing diseases and/or conditions related to dry eye syndrome, psoriasis vulgaris or multiple myeloma.

SUMMARY OF THE INVENTION

In general, the present disclosure relates to the development of novel compounds and/or methods for treating diseases and/or conditions related to dry eye syndrome, psoriasis vulgaris or multiple myeloma.

Accordingly, the first aspect of the present disclosure aims at providing a short synthetic peptide capable of treating diseases and/or conditions related to dry eye syndrome, psoriasis vulgaris or multiple myeloma. The short synthetic peptide consists of the amino acid sequence set forth as $X_1ITYX_2RLKX_3$ (SEQ ID NO: 1), wherein, $X_1$, $X_2$ and $X_3$ are independently any amino acid residues;

$X_3$ is in L- or D-form, while the rest of the amino acid residues are all in L-form; and the N-terminus of the amino acid sequence is acetylated and the C-terminus of the amino acid sequence is amidated.

According to one preferred embodiments, the synthetic peptide has the amino acid sequence of SEQ ID NO: 2 (hereinafter 9-mer). According to other preferred embodiments, the synthetic peptide has the amino acid sequence that is any of SEQ ID NOs: 3, 4, 5, or 6. In one example, the synthetic peptide has the amino acid sequence of SEQ ID NO. 3 (hereinafter 9-mer Da). In another example, the synthetic peptide has the amino acid sequence of SEQ ID NO.7 (hereinafter 9-mer Va). In yet another example, the synthetic peptide has the amino acid sequence of SEQ ID NO. 11 (hereinafter 9-mer Fa).

In a further example, the 9-mer synthetic peptide further comprises additional 3 amino acid residues upstream to its N-terminus, and gives rise to a contiguous peptide of SEQ ID NO: 6 (hereinafter "12-mer").

In further examples, arginine (R) and $X_3$ of SEQ ID NO: 1 are independently in L- or D-form, while the rest of the amino acid residues are all in L-form. In one example, arginine of the 9-mer is in D-form (hereinafter 9-mer DR) (SEQ ID NO:2). In another example, phenylalanine (F) of the 9-mer is in D-form (hereinafter 9-mer DF) (SEQ ID NO:2).

The second aspect of the present disclosure aims at providing a medicament and/or a composition suitable for treating a disease and/or a condition related to dry eye syndrome, psoriasis vulgaris or multiple myelom. The medicament or composition comprises, an effective amount of the synthetic peptide described above, and a pharmaceutically acceptable carrier.

According to some preferred embodiments, the synthetic peptide has the amino acid sequence of SEQ ID NO: 2 (9-mer). According to other preferred embodiments, the synthetic peptide has the amino acid sequence that is any of SEQ ID NOs: 3, 7, 11, or 12. In one example, the synthetic peptide has the amino acid sequence of SEQ ID NO: 3 (hereinafter 9-mer Da). In another example, the synthetic peptide has the amino acid sequence of SEQ ID NO: 7 (hereinafter 9-mer Va). In yet another example, the synthetic peptide has the amino acid sequence of SEQ ID NO: 11 (hereinafter 9-mer Fa).

In a further example, the 9-mer synthetic peptide further comprises additional 3 amino acid residues upstream to its N-terminus, and gives rise to a contiguous peptide of SEQ ID NO: 12 (hereinafter "12-mer").

The disease and/or condition related to angiogenesis treatable by the present medicament or composition is dry eye syndrome, psoriasis vulgaris or multiple myeloma.

According to some embodiments, the present medicament or composition is suitable for treating the ocular disease, such as dry eye syndrome.

According to some embodiments, the present medicament or composition is suitable for treating skin inflammation, particularly, psoriasis vulgaris.

According to some embodiments, the present medicament or composition is suitable for treating tumor, particularly, multiple myeloma.

The medicament or composition of the present disclosure may be administered to the subject via intravascular delivery (e.g., injection or infusion), oral, enteral, rectal, pulmonary (e.g., inhalation), nasal, topical (including transdermal, buccal and sublingual), intravesical, intravitreal, intraperitoneal, vaginal, brain delivery (e.g., intracerebroventricular, and intracerebral), CNS delivery (e.g., intrathecal, perispinal, and intra-spinal) or parenteral (e.g., subcutaneous, intramuscular, intravenous, and intradermal), transmucosal administration or administration via an implant, or other delivery routes known in the art.

The third aspect of the present disclosure is thus directed to a method of treating a subject suffering from a disease and/or a condition related to dry eye syndrome, psoriasis vulgaris or multiple myeloma. The method comprises the step of, administering to the subject a medicament or a composition of the present disclosure described above for ameliorating or alleviating symptoms related to the diseases and/or conditions related to dry eye syndrome, psoriasis vulgaris or multiple myeloma.

In all embodiments, the subject is a human.

In preferred embodiments, the synthetic peptide of the present disclosure is administered in an amount of 0.01-100 mg/Kg to the subject.

The details of one or more embodiments of the invention are set forth in the accompanying description below. Other features and advantages of the invention will be apparent from the detail descriptions, and from claims.

DESCRIPTION OF THE INVENTION

Figure 1:
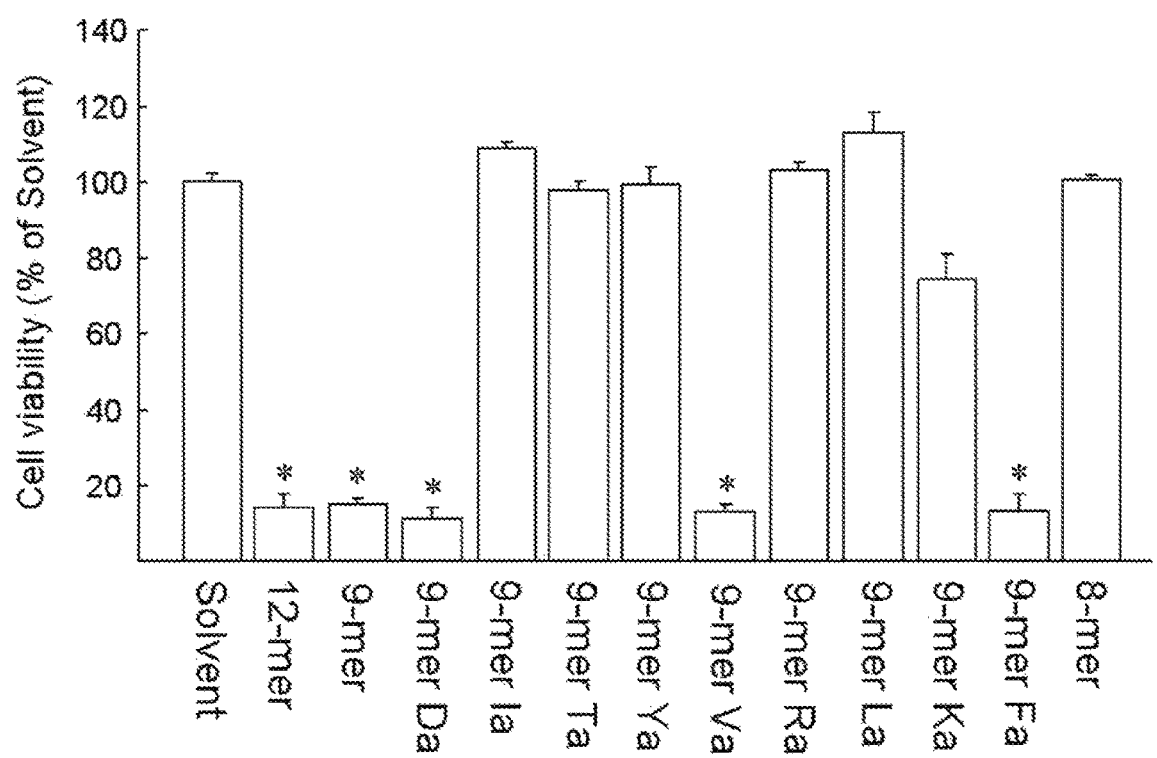
FIG. 1 illustrates the effects of the 9-mer peptide (SEQ ID NO:2) and its alanine substituted analogues on the viability of RPMI8226 cells in accordance with one embodiment of the present disclosure.

The detailed description provided below in connection with the appended drawings is intended as a description of the present examples and is not intended to represent the only forms in which the present example may be constructed or utilized. The description sets forth the functions of the example and the sequence of steps for constructing and operating the example. However, the same or equivalent functions and sequences may be accomplished by different examples.

1. Definitions

For convenience, certain terms employed in the context of the present disclosure are collected here. Unless defined otherwise, all technical and scientific terms used herein have the same meaning as commonly understood by one of the ordinary skill in the art to which this invention belongs.

As used herein, the term "peptide" denotes a polymer of amino acid residues. By the term "synthetic peptide" as used herein, it is meant a peptide which does not comprise an entire naturally occurring protein molecule. The peptide is "synthetic" in that it may be produced by human intervention using such techniques as chemical synthesis, recombinant genetic techniques, or fragmentation of whole antigen or the like. Throughout the present disclosure, the positions of any specified amino acid residues within a peptide are numbered starting from the N terminus of the peptide. When amino acids are not designated as either D- or L-amino acids, the amino acid is either an L-amino acid or could be either a D- or L-amino acid, unless the context requires a particular isomer. Further, the notation used herein for the polypeptide amino acid residues are those abbreviations commonly used in the art.

As discussed herein, minor variations in the amino acid sequences of proteins/peptides are contemplated as being encompassed by the presently disclosed and claimed inventive concept(s), providing that the variations in the amino acid sequence maintain at least 90%, such as at least 70%, 71%, 72%, 73%, 75%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% and 99%. The present synthetic peptide may be modified specifically to alter a feature of the peptide unrelated to its physiological activity. For example, certain amino acids can be changed and/or deleted without affecting the physiological activity of the peptide in this study (i.e., its ability to treat angiogenesis related diseases and/or conditions). In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) nonpolar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the peptide derivative.

Fragments or analogs of proteins/peptides can be readily prepared by those of ordinary skill in the art. Preferred amino- and carboxy-termini of fragments or analogs occur near boundaries of functional domains. In one example, one amino acid residue (e.g., aspartate, valine or phenylalanine) of the present synthetic peptide is conservatively replaced by non-polar amino acid residue (e.g., by alanine). In other examples, one amino acid residue of the present synthetic peptide is conservatively replaced by its D-form amino acid residue, for example, L-form arginine and L-form phenylalanine are respectively replaced by the corresponding D-form residues.

The term "treatment" as used herein are intended to mean obtaining a desired pharmacological and/or physiologic effect, e.g., delaying or inhibiting cancer growth or ameliorating injury to the corneal surface (e.g., dry eye syndrome) or skin (e.g., psoriasis vulgaris). The effect may be prophylactic in terms of completely or partially preventing a disease or symptom thereof and/or therapeutic in terms of a partial or complete cure for a disease and/or adverse effect attributable to the disease. "Treatment" as used herein includes preventative (e.g., prophylactic), curative or palliative treatment of a disease in a mammal, particularly human; and includes: (1) preventative (e.g., prophylactic), curative or palliative treatment of a disease or condition (e.g., a cancer or heart failure) from occurring in an individual who may be pre-disposed to the disease but has not yet been diagnosed as having it; (2) inhibiting a disease (e.g., by arresting its development); or (3) relieving a disease (e.g., reducing symptoms associated with the disease).

The term "administered", "administering" or "administration" are used interchangeably herein to refer a mode of delivery, including, without limitation, intravenously, intramuscularly, intraperitoneally, intraarterially, intracranially, or subcutaneously administering an agent (e.g., a compound or a composition) of the present invention. In some embodiments, the synthetic peptide of the present disclosure and/or its analogues are formulated into eye drops for direct application on the corneal surface. In other embodiments, the synthetic peptide of the present disclosure and/or its analogues are formulated into skin ointments or lotions for direct application on the skin. In further embodiments, the synthetic peptide of the present disclosure and/or its analogues are formulated into powders for mixed with suitable carrier (e.g., buffer solution) before use, such as intravenous injection.

The term "an effective amount" as used herein refers to an amount effective, at dosages, and for periods of time necessary, to achieve the desired result with respect to the treatment of a disease. For example, in the treatment of dry eye disease, an agent (i.e., a compound, a synthetic peptide, or a nucleic acid encoding a therapeutic peptide) which decrease, prevents, delays or suppresses or arrests any symptoms of the dry eye disease would be effective. Similarly, in the treatment of psoriasis vulgaris, an agent (i.e., a compound, a synthetic peptide, or a nucleic acid encoding a therapeutic peptide) which decrease, prevents, delays or suppresses or arrests any symptoms of the psoriatic skin would be effective. An effective amount of an agent is not required to cure a disease or condition but will provide a treatment for a disease or condition such that the onset of the disease or condition is delayed, hindered or prevented, or the disease or condition symptoms are ameliorated. The effective amount may be divided into one, two or more doses in a suitable form to be administered at one, two or more times throughout a designated time period.

The term "subject" or "patient" is used interchangeably herein and is intended to mean a mammal including the human species that is treatable by the synthetic peptide and/or method of the present invention. The term "mammal" refers to all members of the class Mammalia, including humans, primates, domestic and farm animals, such as rabbit, pig, sheep, and cattle; as well as zoo, sports or pet animals; and rodents, such as mouse and rat. Further, the term "subject" or "patient" intended to refer to both the male and female gender unless one gender is specifically indicated. Accordingly, the term "subject" or "patient" comprises any mammal which may benefit from the treatment method of the present disclosure. Examples of a "subject" or "patient" include, but are not limited to, a human, rat, mouse, guinea pig, monkey, pig, goat, cow, horse, dog, cat, bird and fowl. In an exemplary embodiment, the patient is a human.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in the respective testing measurements. Also, as used herein, the term "about" generally means within 10%, 5%, 1%, or 0.5% of a given value or range. Alternatively, the term "about" means within an acceptable standard error of the mean when considered by one of ordinary skill in the art. Other than in the operating/working examples, or unless otherwise expressly specified, all of the numerical ranges, amounts, values and percentages such as those for quantities of materials, durations of times, temperatures, operating conditions, ratios of amounts, and the likes thereof disclosed herein should be understood as modified in all instances by the term "about." Accordingly, unless indicated to the contrary, the numerical parameters set forth in the present disclosure and attached claims are approximations that can vary as desired. At the very least, each numerical parameter should at least be construed in light of the number of reported significant digits and by applying ordinary rounding techniques.

The singular forms "a", "and", and "the" are used herein to include plural referents unless the context clearly dictates otherwise.

2. Detail Description of Preferred Embodiments

The present disclosure is based, at least in part, on the discovery of short synthetic peptides that are capable of treating and/or preventing a subject from developing a disease or a condition related to angiogenesis. Accordingly, this invention provides method and composition comprising the newly identified synthetic peptides for the treatment and/or prophylaxis of a disease or a condition related to angiogenesis.

2.1 the Present Synthetic Peptides

The short synthetic peptide of the present disclosure consists of the amino acid sequence set forth as $X_1ITYX_2RLKX_3$ (SEQ ID NO: 1), wherein, $X_1$, $X_2$ and $X_3$ are independently any amino acid residues;
$X_3$ is in L- or D-form, while the rest of the amino acid residues are all in L-form; and
the N-terminus of the amino acid sequence is acetylated and the C-terminus of the amino acid sequence is amidated.

According to one preferred embodiment, the synthetic peptide of the present disclosure has the amino acid sequence of DITYVRLKF (SEQ ID NO: 2, 9-mer).

According to other embodiments, the 9-mer synthetic peptide (SEQ ID NO:2) may have a conservative substitution therein, thereby give rise to an analogue having the amino acid sequence that is any of SEQ ID Nos: 3, 7, or 11.

According to another preferred embodiment, the 9-mer synthetic peptide (SEQ ID NO:2) further comprises 3 additional amino acid residues upstream to its N-terminus, and thereby gives rise to a contiguous peptide of KAFDITYVR-LKF (SEQ ID NO: 12, hereinafter "12-mer").

In still further example, the 9-mer synthetic peptide (SEQ ID NO:2) may include at least one D-form amino acid residues therein, and thereby give rise to its D-form analogues.

The present synthetic peptides are described in detail in Table 1 below.

TABLE 1

The present synthetic peptides

| Peptide Name | Amino Acid Sequence | SEQ ID NO |
|---|---|---|
| 9-mer | NH$_2$-Asp-Ile-Thr-Tyr-Val-Arg-Leu-Lys-Phe-COOH<br>DITYVRLKF | 2 |
| 9-mer Da | NH$_2$-Ala-Ile-Thr-Tyr-Val-Arg-Leu-Lys-Phe-COOH<br>AITYVRLKF | 3 |
| 9-mer Ia | NH$_2$-Asp-Ala-Thr-Tyr-Val-Arg-Leu-Lys-Phe-COOH<br>DATYVRLKF | 4 |
| 9-mer Ta | NH$_2$-Asp-Ile-Ala-Tyr-Val-Arg-Leu-Lys-Phe-COOH<br>DIAYVRLKF | 5 |
| 9-mer Ya | NH$_2$-Asp-Ile-Thr-Ala-Val-Arg-Leu-Lys-Phe-COOH<br>DITAVRLKF | 6 |
| 9-mer Va | NH$_2$-Asp-Ile-Thr-Tyr-Ala-Arg-Leu-Lys-Phe-COOH<br>DITYARLKF | 7 |
| 9-mer Ra | NH$_2$-Asp-Ile-Thr-Tyr-Val-Ala-Leu-Lys-Phe-COOH<br>DITYVALKF | 8 |
| 9-mer La | NH$_2$-Asp-Ile-Thr-Tyr-Val-Arg-Ala-Lys-Phe-COOH<br>DITYVRAKF | 9 |
| 9-mer Ka | NH$_2$-Asp-Ile-Thr-Tyr-Val-Arg-Leu-Ala-Phe-COOH<br>DITYVRLAF | 10 |
| 9-mer Fa | NH$_2$-Asp-Ile-Thr-Tyr-Val-Arg-Leu-Lys-Ala-COOH<br>DITYVRLKA | 11 |
| 12-mer | NH$_2$-Lys-Ala-Phe-Asp-Ile-Thr-Tyr-Val-Arg-Leu-Lys-Phe-COOH<br>KAFDITYVRLKF | 12 |
| 8-mer | NH$_2$-Ile-Thr-Tyr-Val-Arg-Leu-Lys-Ala-COOH<br>ITYVRLKA | 13 |
| 9-mer DD | NH$_2$-(D-Asp)Ile-Thr-Tyr-Val-Arg-Leu-Lys-Phe-COOH<br>DITYVRLKF | 2 |

TABLE 1-continued

The present synthetic peptides

| Peptide Name | Amino Acid Sequence | SEQ ID NO |
|---|---|---|
| 9-mer DI | NH$_2$-Asp-(D-Ile)-Thr-Tyr-Val-Arg-Leu-Lys-Phe-COOH<br>DITYVRLKF | 2 |
| 9-mer DT | NH$_2$-Asp-Ile-(D-Thr)-Tyr-Val-Arg-Leu-Lys-Phe-COOH<br>DITYVRLKF | 2 |
| 9-mer DY | NH$_2$-Asp-Ile-Thr-(D-Tyr)-Val-Arg-Leu-Lys-Phe-COOH<br>DITYVRLKF | 2 |
| 9-mer DV | NH$_2$-Asp-Ile-Thr-Tyr-(D-Val)-Arg-Leu-Lys-Phe-COOH<br>DITYVRLKF | 2 |
| 9-mer DR | NH$_2$-Asp-Ile-Thr-Tyr-Val-(D-Arg)-Leu-Lys-Phe-COOH<br>DITYVRLKF | 2 |
| 9-mer DL | NH$_2$-Asp-Ile-Thr-Tyr-Val-Arg-(D-Leu)-Lys-Phe-COOH<br>DITYVRLKF | 2 |
| 9-mer DK | NH$_2$-Asp-Ile-Thr-Tyr-Val-Arg-Leu-(D-Lys)-Phe-COOH<br>DITYVRLKF | 2 |
| 9-mer DF | NH$_2$-Asp-Ile-Thr-Tyr-Val-Arg-Leu-Lys-(D-Phe)-COOH<br>DITYVRLKF | 2 |

The bold letter in any sequence indicates that particular amino acid is in D-form.

According to preferred embodiments, isoleucine (I), threonine (T), tyrosine (Y), arginine (R), leucine (L), and lysine (K) residues of SEQ ID NO: 1 must not be replaced by other amino acid residues, or else the synthetic peptide will lose its bioactivity towards dry-eye syndrome, psoriasis vulgaris and/or multiple myeloma. Accordingly, $X_1$, $X_2$ and $X_3$ of SEQ ID NO: 1 may be independently any amino acid residues. In one embodiment, $X_1$ is alanine (A), $X_2$ is valine (V), $X_3$ is phenylalanine, and the synthetic peptide has the amino acid sequence of SEQ ID NO: 3 (hereinafter "9-mer Da"). In another embodiment, $X_1$ is aspartate, $X_2$ is alanine (A), and the synthetic peptide has the amino acid sequence of SEQ ID NO: 7 (hereinafter "9-mer Va"). In still another embodiment, $X_1$ is aspartate, $X_2$ is valine (V), $X_3$ is alanine (A), and the synthetic peptide has the amino acid sequence of SEQ ID NO: 11 (hereinafter "9-mer Fa")

According to further embodiments, at least one D-form amino acid residues is included in the 9-mer synthetic peptide (SEQ ID NO:2), particularly the amino acid residue at position 9, which gives rises to D-form analogues of the 9-mer as described in Table 1 above. In one specific example, phenylalanine (F) of the 9-mer synthetic peptide (SEQ ID NO:2) is in D-form, while the rest of the amino acid residues are in L-form.

The present synthetic peptide may be synthesized in accordance with any standard peptide synthesis protocol in the art. In one embodiment, the present synthetic peptides were synthesized by use of a solid-phase peptide synthesizer (ABI433A peptide synthesizer, Applied Biosystems Inc., Life Technologies Corp., Foster City, Calif., USA) in accordance with the manufacturer's protocols.

Alternatively, the present synthetic peptides may be prepared using recombinant technology. For example, one can clone a nucleic acid encoding the present peptide in an expression vector, in which the nucleic acid is operably linked to a regulatory sequence suitable for expressing the present peptide in a host cell. One can then introduce the vector into a suitable host cell to express the peptide. The expressed recombinant polypeptide can be purified from the host cell by methods such as ammonium sulfate precipitation and fractionation column chromatography. A peptide thus prepared can be tested for its activity according to the method described in the examples below.

The above-mentioned nucleic acids or polynucleotide can be delivered by the use of polymeric, biodegradable microparticle or microcapsule delivery devices known in the art. Another way to achieve uptake of the nucleic acid in a host is using liposomes, prepared by standard methods. The polynucleotide can be incorporated alone into these delivery vehicles or co-incorporated with tissue-specific antibodies. Alternatively, one can prepare a molecular conjugate composed of a plasmid or other vector attached to poly-L-lysine by electrostatic or covalent forces. Alternatively, tissue specific targeting can be achieved by the use of tissue-specific transcriptional regulatory elements that are known in the art. Delivery of "naked DNA" (i.e., without a delivery vehicle) to an intramuscular, intradermal, or subcutaneous site is another means to achieve in vivo expression.

The present synthetic peptide may be modified at its N-terminus or C-terminus. Examples of N-terminal modifications include, but are not limited to, N-glycated, N-alkylated, and N-acetylated amino acid. A terminal modification can include a pegylation. An example of C-terminal modification is a C-terminal amidated amino acid. Alternatively, one or more peptide bond may be replaced by a non-peptidyl linkage, the individual amino acid moieties may be modified through treatment with agents capable of reacting with selected side chains or terminal residues.

Various functional groups may also be added at various points of the synthetic peptide that are susceptible to chemical modification. Functional groups may be added to the termini of the peptide. In some embodiments, the function groups improve the activity of the peptide with regard to one or more characteristics, such as improving the stability, efficacy, or selectivity of the synthetic peptide; improving the penetration of the synthetic peptide across cellular membranes and/or tissue barrier; improving tissue localization; reducing toxicity or clearance; and improving resistance to expulsion by cellular pump and the like. Non-limited examples of suitable functional groups are those that facilitate transport of a peptide attached thereto into a cell, for example, by reducing the hydrophilicity and increasing the lipophilicity of the peptide, these functional groups may optionally and preferably be cleaved in vivo, either by hydrolysis or enzymatically, inside the cell. Hydroxy protecting groups include esters, carbonates and carbamate protecting groups. Amine protecting groups include alkoxy and aryloxy carbonyl groups. Carboxylic acid protecting groups include aliphatic, benzylic and aryl esters. In some optional embodiments, the carboxylic acid group in the side chain of the aspartic acid (D) of the present synthetic peptide is protected, preferably, by a methyl, ethyl, benzyl, or substituted to benzyl ester.

A "peptidomimetic organic moiety" can optionally be substituted for amino acid residues in the present synthetic peptide both as conservative and as non-conservative substitutions. The peptidomimetic organic moieties optionally and preferably have steric, electronic or configuration properties similar to the replaced amino acid and such peptidomimetics are used to replace amino acids in the essential positions, and are considered conservative substitutions. Peptidomimetics may optionally be used to inhibit degradation of peptides by enzymatic or other degradative processes. The peptidomimetics can optionally and preferably be produced by organic synthetic techniques. Non-limiting examples of suitable peptidomimetics include isosteres of amide bonds, 3-amino-2-propenidone-6-carboxylic acid, hydroxyl-1,2,3,4-tetrahydro-isoquinoline-3-carboxylate, 1,2,3,4-tetrahydro-isoquinoline-3-carboxylate, and histidine isoquinolone carboxylic acid.

Any part of the synthetic peptide may optionally be chemically modified, such as by the addition of functional groups. The modification may optionally be performed during the synthesis of the present peptide. Non-limiting exemplary types of the modification include carboxymethylation, acylation, phosphorylation, glycosylation or fatty acylation. Ether bonds can optionally be used to join the serine or threonine hydroxyl to the hydroxyl of a sugar. Amide bonds can optionally be used to join the glutamate or aspartate carboxy groups to an amino group of a sugar. Acetal and ketal bonds can also optionally be formed between amino acids and carbon hydrates.

2.2 Compositions for the Treatment and/or Prophylaxis of Diseases and/or Conditions Related to Dry Eye Syndrome, Psoriasis Vulgaris or Multiple Myeloma The present synthetic peptides are suitable for treating a subject suffering from a disease and/or a condition related to dry eye syndrome, psoriasis vulgaris or multiple myeloma; or preventing a subject from developing the disease and/or condition related to dry eye syndrome, psoriasis vulgaris or multiple myeloma.

Accordingly, a further aspect of the present disclosure is to provide a medicament comprising the present synthetic peptide for treating a disease and/or a condition related to dry eye syndrome, psoriasis vulgaris or multiple myeloma.

In one embodiment, the medicament is for the treatment of tumor, particularly, multiple myeloma, in which after treatment, the volume, the growth rate, and/or the metastasis of the tumor are reduced or decreased.

In another embodiment, the medicament is for the treatment of an ocular disease, particularly dry eye syndrome.

In yet another embodiment, the medicament is for the treatment of a skin disease, particularly psoriasis vulgaris.

The medicament is manufactured by mixing suitable amount of the present synthetic peptide with a pharmaceutically acceptable carrier, excipient or stabilizer into a composition. In particular embodiments, the synthetic peptide is selected from the group of peptides as described above, which include but are not limited to, 9-mer (SEQ ID NO: 2), 9-mer Da (SEQ ID NO: 3), 9-mer Va (SEQ ID NO: 7), 9-mer Fa (SEQ ID NO: 11), 9-mer DF (SEQ ID NO: 2), 12-mer (SEQ ID NO: 12), and a combination thereof.

The amount of the peptide present in the medicament or the composition will depend on the peptide used. The peptide typically will be present in the composition in the amount from about 0.001% to about 10% by weight, such as 0.001, 0.005, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, and 10.0% by weight; in particular in an amount from about 0.01% to about 5% by weight, such as 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.9, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, and 5.0% by weight.

Pharmaceutical acceptable carriers, excipients or stabilizers for use with the synthetic peptides are well known in the relevant art, and include but are not limited to non-toxic inert solid, semi-solid, or liquid filler, diluent, encapsulating agent or formulation auxiliary. Typical pharmaceutically acceptable carrier is water or physiological saline. Examples of pharmaceutically acceptable carriers include, but are not limited to, sugars such as lactose, glucose, and sucrose; starches such as corn starch; cellulose and its derivatives such as carboxymethyl cellulose, ethyl cellulose, and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such as propylene glycol; esters such as ethyl oleate and ethyl laurate; agar; buffering agents such as magnesium hydroxide and aluminum hydroxide; alginic acid; as well as other agents such as non-toxic lubricants (e.g., lauryl sulfate and magnesium stearate), coloring agents, releasing agents, flavoring agents, preservatives and antioxidants. The composition may further comprise an anti-biotic or an anti-mycotic agent therein.

Suitable routes of administration of the medicament or the composition of the present invention are intravascular delivery (e.g., injection or infusion), oral, enteral, rectal, pulmonary (e.g., inhalation), nasal, topical (including transdermal, buccal and sublingual), intravesical, intravitreal, intraperitoneal, vaginal, brain delivery (e.g., intracerebroventricular, and intracerebral), CNS delivery (e.g., intrathecal, perispinal, and intra-spinal) or parenteral (e.g., subcutaneous, intramuscular, intravenous, and intradermal), transmucosal administration or administration via an implant, or other delivery routes known in the art.

Pharmaceutical composition suitable for oral administration may be formulated into discrete dosage units such as pills, tablets, lozenges or hard or soft capsules, or as a dispersible powder or granules, or as a solutions or suspension for example, aqueous or oily suspensions, emulsions, syrups, elixirs, or enteral formulas. In one preferred example, the pharmaceutical composition is an eye drop. The composition may be presented in uni-dose or multi-dose containers, such as sealed vials or ampoules, and may be stored in a lyophilized condition requiring the addition of sterile liquid carrier (e.g., water or saline) prior to use.

Pharmaceutical composition suitable for parental administration may be formulated into aqueous or non-aqueous sterile injection by mixing or dispersing the present synthetic peptide with a sterile solvent, such as water, Ringer's solution, saline, 1,3-butanediol, alcohol and etc. Alternatively, fixed oil, fatty acid or synthetic mono- or diglycerides may be used as the solvent. The composition may be sterilized by filtering through a filter.

For topical or transdermal application, the pharmaceutical composition is generally formulated into ointments, pastes, creams, lotions, gels, patches or sprays. Ophthalmic formulations, ear drops, and eye drops are also contemplated within the scope of the invention. According to some embodiments, compositions of the invention are administered topically to the eye. According to other embodiments, the pharmaceutical composition is an ointment for skin use. Depending on the type and severity of the disease, about 1 µg/kg to about 100 mg/kg (e.g., 0.1-50 mg/kg) of the present synthetic peptide is administered to the patient, such as 1, 5, 10, 20, 30, 40, 50, 60, 70, 80, 90, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 900, 910, 920, 930, 940, 950, 960, 970, 980, 990, or 1,000 µg/kg; or 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 mg/kg. A typical daily or weekly dosage might range from about 0.1 mg/Kg to about 50 mg/kg or more, such as 0.1, 0.2, 0.3, 0.4, 0.5, 0.6, 0.7, 0.8, 0.9, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mg/Kg. The doses utilized for any of the above-described purposes of topical administration will generally be administered one to several, e.g., four, six, eight or even more, times per day.

Pharmaceutical composition suitable for pulmonary administration is formulated as find dusts or mists which may be generated by means of metered dose pressurized aerosols, nebulisers or insufflators.

The pharmaceutical composition provided by the invention preferably is presented in the form of a kit. In the present invention, a "kit" is understood as a product containing the synthetic peptide(s) provided by the present invention and/or the additional therapeutic compounds forming the packaged composition such that the transport, storage and simultaneous or successive administration thereof is allowed. Therefore, the kits of the invention can contain one or more sealed ampoules respectively contain the synthetic peptides of the invention, and which can be prepared in a single dose or as multiple doses. The kit can additionally contain a vehicle suitable for solubilizing the synthetic peptides such as aqueous media such as saline solution, Ringer's solution, dextrose and sodium chloride; water-soluble media such as alcohol, polyethylene glycol, propylethylene glycol; and water-insoluble vehicles if necessary. Another component which may be present in the kit is a package which allows maintaining the compositions of the invention within determined limits. Materials suitable for preparing such packages include glass, plastic (polyethylene, polypropylene, polycarbonate and the like), bottles, vials, paper, sachets and the like.

The kit of the invention can additionally contain instructions for the simultaneous, successive or separate administration of the different formulations present in the kit. Therefore, the kit of the invention can further comprise instructions for the simultaneous, successive or separate administration of the different components. Said instructions can be in the form of printed material or in the form of an electronic support which can store the instructions such that they can be read by a subject, such as electronic storage media (magnetic disks, tapes and the like), optical media (CD-ROM, DVD) and the like. The media can additionally or alternatively contain Internet webpages providing said instructions.

2.3 Methods for the Treatment and/or Prophylaxis of Diseases and/or Conditions Related to Dry Eye Syndrome, Psoriasis Vulgaris or Multiple Myeloma As it has been indicated above, the findings described in the present invention are useful for the prevention and/or treatment of diseases and/or conditions related to dry eye syndrome, psoriasis vulgaris or multiple myeloma.

The present invention therefore relates to a method for the prevention and/or treatment of diseases and/or conditions related to dry eye syndrome, psoriasis vulgaris or multiple myeloma, which comprises administering to a subject in need thereof a medicament or a composition described above, which comprises a synthetic peptide consisting of the amino acid sequence set forth as $X_1ITYX_2RLKX_3$ (SEQ ID NO: 1), wherein, $X_1$, $X_2$ and $X_3$ are independently any amino acid residues; and $X_3$ is in L- or D-form, while the rest of the amino acid residues are all in L-form; and a pharmaceutically acceptable carrier.

The medicament and/or composition when administrated to the subject is capable of ameliorating or alleviating the symptoms associated to the diseases and/or conditions related to dry eye syndrome, psoriasis vulgaris or multiple myeloma.

In particular embodiments, the synthetic peptide is selected from the group of peptides described above, which include and are not limited to, 9-mer (SEQ ID NO: 2), 9-mer Da (SEQ ID NO: 3), 9-mer Va (SEQ ID NO: 7), 9-mer Fa (SEQ ID NO: 11), 9-mer DF (SEQ ID NO: 2), 12-mer (SEQ ID NO: 12), and a combination thereof.

According to one embodiment, the present invention is related to a method for treating tumor, particularly, multiple myeloma, which comprises administering to a subject in need thereof a medicament or a composition of the present invention.

According to another embodiment, the present invention is related to a method for treating an ocular disease, particularly, dry eye syndrome, which comprises administering to a subject in need thereof a medicament or a composition of the present invention.

According to another embodiment, the present invention is related to a method for treating a psoriasis vulgaris, which comprises administering to a subject in need thereof a medicament or a composition of the present invention.

The method includes the step of, administering to a subject in need thereof a medicament or a composition of the present invention.

Optionally, the present method may further include administering to the subject an effective amount of an agent selected from the group consisting of an anti-inflammatory agent, an anti-cancer agent, and an antibiotic, for treating diseases and/or conditions related to dry eye syndrome, psoriasis vulgaris or multiple myeloma.

In some examples, the anti-inflammatory agent may be cyclosporine. The anti-cancer agent may be an alkylating agent, an anti-microtubule agent, a topoisomerase inhibitor, or a cytotoxic agent. The antibiotic may be selected from the group consisting of, amikacin, gentamycin, kanamycin, neomycin, netilmicin, streptomycin, tobramycin, teicoplanin, vancomycin, azithromycin, clarithromycin, dirithromycin, erythromycin, roxithromycin, troleanodomycin, amoxicillin, ampicillin, azlocillin, carbenicillin, clozacillin, dicloxacillin, flucozacillin, meziocillin, nafcillin, penicillin, piperacillin, ticarcillin, bacitracin, colistin, polymyxin B, ciprofloxacin, enoxacin, gatifloxacin, levofloxacin, lomefloxacin, moxifloxacin, norfloxacin, oflazacin, trovafloxacin, mafenide, sulfacetamide, sulfamethizole, sulfasalazine, sulfisoxazole, trimethoprim, cotrimoxazole, demeclocycline, soxycycline, minocycline, oxytetracycline, and tetracycline.

In all embodiments, the subject suitable for treatment is a human.

The present invention will now be described more specifically with reference to the following embodiments, which are provided for the purpose of demonstration rather than limitation.

EXAMPLES

Materials and Methods

Materials

RPMI1640 medium, trypsin-EDTA, fetal bovine serum (FBS), antibiotic-antimicotic solutions and trypsin were purchased from Invitrogen (Carlsbad, Calif., USA). Carboxymethylcellulose sodium (CMC), dimethyl sulfoxide (DMSO), and 5-bromo-2'-deoxyuridine (BrdU) were all from Sigma-Aldrich (St. Louis, Mo.). 3-(4,5-dimethylthiazol-2-yl)-2,5-diphenyl tetrazolium bromide (MTT) was from Merck (Catalog number 1.11714.0001). Anti-BrdU antibody was purchased from GeneTex (San Antonio, Ill., USA). Short synthetic peptides including 12-mer (KAFDITYVRLKF) (SEQ ID NO: 12), 9-mer (DITYVRLKF) (SEQ ID NO: 2), 8-mer (ITYVRLFK) (SEQ ID NO: 13), alanine-substituted peptides and D-peptides were synthesized, modified by acetylation at the NH2 termini and amidation at the COOH termini for stability, and characterized by mass spectrometry (>90% purity), to order from GenScript (Piscataway, N.J.) All peptides were synthesized by GenScript (Piscataway, N.J., USA), in which each peptide was modified by acetylation at the NH2 termini and amidation at the COOH termini to improve its stability, and was subsequently characterized using mass spectrometry (>95% purity).

Cell Culture

The multiple myeloma line RPMI8226 or rat Raw264.7 macrophages were cultivated in complex medium (RPMI1640) supplemented with 10% (vol/vol) heat-inactivated fetal calf serum (Invitrogen), 50 μg/mL penicillin, 50 μg/mL streptomycin, and 2 mM L-glutamine at 37° C. in a 5% $CO_2$ atmosphere MTT Assay RPMI8226 cells or U266 cells were cultured in serum-free RPMI1640 medium for 24 h, and then cells seeded in 48-well culture plates ($3 \times 10^5$ cells/well) and cultured in 0.5 ml fresh serum-free RPMI1640 medium containing 20 μM peptide for further 24 h. The cell viability was determined by the MTT assay.

50 μL of the MTT stock solution (5 mg MTT dissolved in 1 ml of sterile PBS) was added to each well, and 50 μL of the MTT stock solution was added to 500 μL of medium alone and used as a negative control. Each sample was Incubates at 37° C. for 4 hours. Aliquots (450 μl) from each sample were taken to a new well of 48-well culture plate, adding 100 μL DMSO, mixing thoroughly using the pipette and reacted at 37° C. for 20 min and absorbance was measured at 570 nm.

Trypan Blue Exclusion

The cells were examined under a microscope with the aid of a hemacytometer, in which 0.1 mL of trypan blue stock solution (0.4% solution of trypan blue in isotonic salt buffer solution, pH 7.2) was added to 1 mL cell suspension, and loaded therein. The number of blue staining cells (considered non-viable) and the number of total cells were respectively counted. Cell viability should be at least 95% for healthy log-phase cultures.

Evaluation of Apoptosis

Annexin V/propidium iodide (PI) staining was performed using flow cytometry according to the manufacturer's guidelines (Annexin V-FITC Apoptosis Detection kit; Roche). Briefly, $0.5 \times 10^6$ cells were washed in ice-cold PBS without $Ca^{2+}$ or $Mg^{2+}$ (Life Technologies). The cells were then re-suspended in 100 μl of binding buffer and incubated with 5.0 μl of PI and 2.0 μl of annexin V-fluorescein isothiocyanate for 15 min in the dark at room temperature. Flow cytometric analysis was immediately performed using a FACScalibur Instrument (Becton Dickinson).

Dry Eye Animal Model

Animals

C57BL/6 mice (7-8 weeks old, each weighted about 18 to 25 g) were used in this model system. All mice were maintained in the animal facility in accordance with the procedures approved by Mackay Memorial Hospital Review Board (Taiwan, R.O. C.). All animal experimental procedures were conducted according to the ARVO Statement for the Use of Animals in Ophthalmic and Vision Research.

Dry Eye Induction

Dry eyes were induced by placing mice in a controlled environment chamber (CEC) for 14 days in accordance with procedures previously described by Barabino et al (IVOS (2005) 46(8), 2766-2771). Mice placed in the CEC were exposed to a condition, in which relative humidity (RH) was maintained at <25%, temperature at 20-22° C., and airflow at about 15 L/min, for 12 hours per day. Control mice were kept in a normal environment (RH>50%, no air flow, temperature of 20-22° C.) for the same duration.

Treatment

A common artificial tear formulation, 1% carboxymethylcelllulose (CMC) dissolved in balanced salt solution (BSS) was used as the peptide vehicle. Peptide (50 μM) or 1% CMC vehicle was topically administered to eyes three times a day, for 4 days.

Fluorescein Eye Stain Test for Detecting Corneal Injuries

Corneal epithelial injury was determined by staining with topical fluorescein (100 mg/ml or 10%; FLUORESCITE™, Alcon Laboratories). For dosing, topical fluorescein (0.6 μL of 0.5% sodium fluorescein dissolved in 4.4 μL BSS per eye) was applied via a micro-pipette to the lateral canthus for 15 sec. Corneal fluorescein staining was examined with a slit-lamp biomicroscope under cobalt blue light and photographed with a digital camera. Data is presented as mean±SD. Dye staining of the cornea was scored in a blinded manner as follows: score 0 for no punctuate staining; score 1 when less than one third of the cornea was stained; score 2 when two thirds or less was stained; and score 3 when more than two thirds was stained.

Measurement of Tear Production

Tear production was measured with phenol red-impregnated cotton threads (Zone-Quick; Oasis, Glendora, Calif.). The validity of this test in mice was performed as previously described (Dursun et al., Invest Ophthalmol Vis Sci. 2002; 43:632-8). The threads were held with jeweler forceps and placed in the lateral canthus for 60 seconds. The tear production expressed in millimeters of thread wet by the tear and turned red.

Experimental Psoriasis Vulgaris-Like Skin Inflammation Model

BALB/c mice (8-weeks old females; n=42) were used in this model system. It has been demonstrated that treating mouse skin with Imiquimod (IMQ) would result in a psoriasis vulgaris-like skin inflammation (van der Fits et al., J Immunol. 2009; 182:5836-45). Accordingly, in this model, each BALB/c mice received a daily topical dose (62.5 mg) of commercially available IMQ cream (Imiquimod Cream 5% w/w, Aldara™) on the shaved back and the right ear for 6 consecutive days (n=6); whereas the control mice (normal group) were treated with a control cream (n=6). For treatment, each test peptide was mixed with IMQ cream to give a concentration of 25 μM (n=6 per group). Keratinocyte proliferation was determined by BrdU incorporation. BrdU (Sigma-Aldrich) was reconstituted in DMSO as a stock solution of 80 mM. 10 μl of BrdU mixed with 90 μl of PBS was intraperitoneally injected into each mouse for 24 hr prior to euthanasia.

Histology and Immunohistochemistry and Quantification

Back skin of the mouse was fixed overnight in 4% paraformaldehyde, dehydrated with graded ethanol series, and paraffinized. Fixed samples were deparaffinized in xylene and rehydrated in a graded series of ethanol. Tissues were sliced into 5-μm sections. General histology was performed using hematoxylin and eosin (H&E) (Merck, Rayway, N.J., USA).

Slides were blocked with 10% goat serum for 60 min and then incubated with primary antibody against BrdU (1:50 dilution; GTX42641) for 3 hr at RT. The slides were then incubated with peroxidase-labeled donkey immunoglobulin for 30 min and then incubated with chromogen substrate (3,3'-diaminobenzidine) for 2 min before counterstaining with hematoxylin. Quantification was estimated based on high quality images (1208×960 pixels buffer) captured using a Nikon Eclipse 80i light microscope.

Statistics

Results were expressed as the mean±standard error of the mean (SEM). 1-way ANOVA was used for statistical comparisons. $P<0.05$ was considered significant.

Example 1 Effects of 9-Mer and its Analogues on Cell Viability

In this example, the efficacy of 9-mer (DITYVRLKF, SEQ ID NO: 2) peptide of the present invention and its analogues on myeloma RPMI 8226 cell viability were investigated. Four types of 9-mer analogues were produced. The first type of analogues, which included 9-mer Da, 9-mer Ia, 9-mer Ta, 9-mer Ya, 9-mer Va, 9-mer Ra, 9-mer La, 9-mer Ka, and 9-mer Fa peptides (SEQ ID NOs: 3 to 11), were produced by respectively replacing the specified amino acids of the 9-mer with alanine. For example, 9-mer Da (SEQ ID NO: 3) represented the 9-mer analogue, in which the aspartate (D) residue was replaced by alanine (A). Similarly, 9-mer Ia (SEQ ID NO: 4), 9-mer Ta (SEQ ID NO: 5), 9-mer Ya (SEQ ID NO: 6), 9-mer Va (SEQ ID NO: 7), 9-mer Ra (SEQ ID NO: 8), 9-mer La (SEQ ID NO: 9), 9-mer Ka (SEQ ID NO: 10), and 9-mer Fa (SEQ ID NO: 11) peptides represented the 9-mer analogues, in which the isoleucine (I), threonine (T), tyrosine (Y), valine (V), arginine (R), leucine (L), lysine (K) and phenylalanine (F) residues of the 9-mer (SEQ ID NO: 2) were respectively replaced by alanine. The second type of analogues, which included 9-mer DD, 9-mer DI, 9-mer DT, 9-mer DY, 9-mer DV, 9-mer DR, 9-mer DL, 9-mer DK and 9-mer DF (those are SEQ ID NO: 2), were produced by respectively replacing the specified amino acids of the 9-mer (SEQ ID NO: 2) with corresponding D-form amino acids. For example, DD represented the 9-mer analogue, in which the aspartate (D) residue was replaced by D-form aspartate. Similarly, 9-mer DI, 9-mer DT, 9-mer DY, 9-mer DV, 9-mer DR, 9-mer DL, 9-mer DK and 9-mer DF (those are SEQ ID NO: 2) represented the 9-mer analogues, in which the isoleucine (I), threonine (T), tyrosine (Y), valine (V), arginine (R), leucine (L), lysine (K) and phenylalanine (F) residues of the 9-mer (SEQ ID NO:2) were respectively replaced by the corresponding D-form amino acid residues. The third type of 9-mer analogue was the 12-mer peptide, in which additional 3 amino acid residues were added to the N-terminal of the 9-mer (SEQ ID NO:2), thereby gave rise to the 12-mer peptide (KAFDITYVRLKF, SEQ ID NO: 12). The fourth type of 9-mer analogue was the 8-mer peptide, in which the aspartate (D) residue of the 9-mer was deleted, thereby gave rise to the 8-mer peptide (ITYVRLKF, SEQ ID NO: 13).

Figure 2:
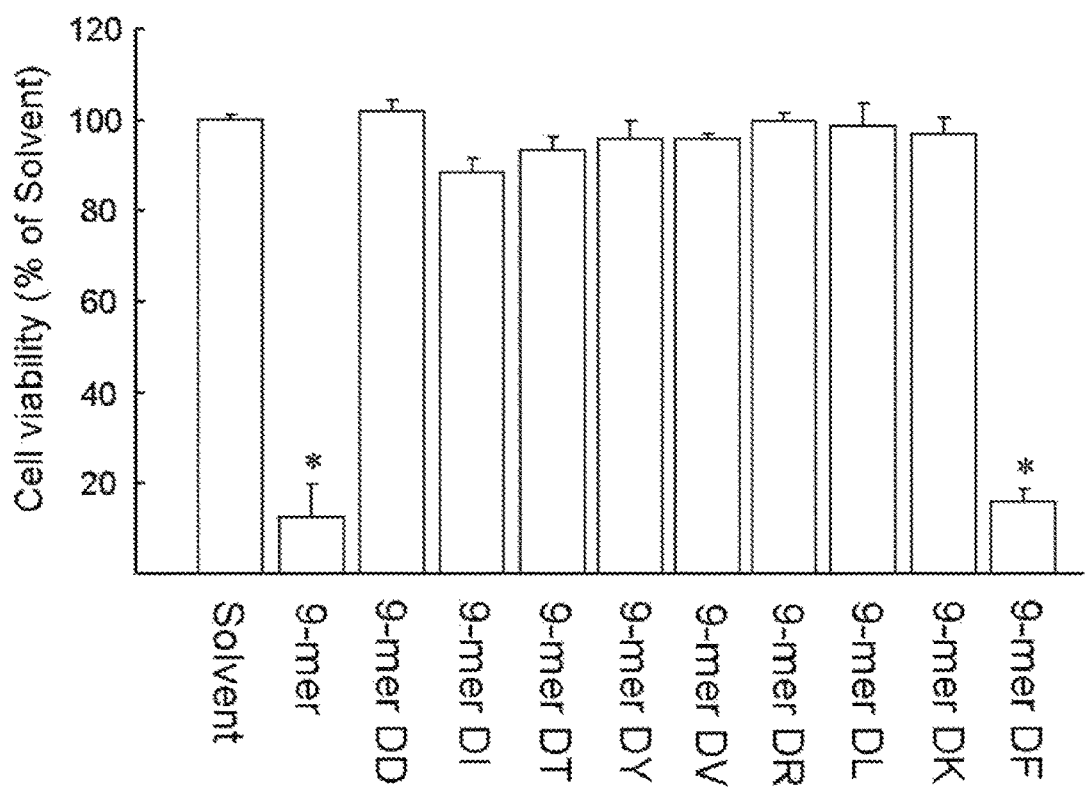
FIG. 2 illustrates the effects of the 9-mer peptide (SEQ ID NO:2) and its D-form amino acid substituted analogues on the viability of RPMI8226 cells in accordance with another embodiment of the present disclosure.

The effects of 9-mer (SEQ ID NO: 2) and its analogues on cell viability as determined by MTT assay were illustrated in FIGS. 1 to 2.

As evidenced from the data depicted in FIG. 1, both 12-mer (SEQ ID NO: 12) and 9-mer (SEQ ID NO: 2) successfully suppressed myeloma RPMI 8226 cell viability; however, alanine substitution for the 9-mer residues at positions 2, 3, 4, 6, 7, and 8 (i.e., 9-mer Ia (SEQ ID NO: 4), 9-mer Ta (SEQ ID NO: 5), 9-mer Ya (SEQ ID NO: 6), 9-mer Ra (SEQ ID NO: 8), 9-mer La (SEQ ID NO: 9), and 9-mer Ka (SEQ ID NO: 10) peptides) caused loss of the inhibitory activity of 9-mer (SEQ ID NO: 2), suggesting amino acid residues in any of these positions were essential for the bioactivity of the 9-mer (SEQ ID NO: 2). Notably, the alanine substitution for the 9-mer residues at positions 1, 5 and 9 (i.e., 9-mer Da (SEQ ID NO: 3), 9-mer Va (SEQ ID NO: 7) and 9-mer Fa (SEQ ID NO: 11) peptides) could sustain part of the inhibitory activity of the 9-mer (SEQ ID NO: 2), suggesting amino acid residues at these 3 positions were non-essential to the inhibitory function of 9-mer (SEQ ID NO: 2).

On the other hand, the 9-mer analogues, in which D-form amino acid substitutions were made, it was unexpectedly found that 9-mer residues at positions 1 to 8 resulted in loss of the bioactivity of the 9-mer (SEQ ID NO: 2). Notably, the 9-mer DF peptide (i.e., D-amino acid substitution for the 9-mer residues at position 9) (SEQ ID NO: 2), had similar activity compared with that of the 9-mer (SEQ ID NO: 2), indicating that D-form substitution can sustain peptide activity (FIG. 2).

Taken together, the result indicate that the 9-mer (SEQ ID NO: 2) and the 12-mer (SEQ ID NO: 12) are both effective in suppressing myeloma cell viability, with 12-mer (SEQ ID NO: 12) being more potent at lower dose. Further, the amino acid residues at positions 1, 5, and 9 of the 9-mer peptide (SEQ ID NO: 2) may be replaced by other amino acid residues; and amino acid residues at position 9 of the 9-mer (SEQ ID NO: 2) can be either L- or D-form, whereas the rest of the amino acid residues must remain in L-form, so as to keep the bioactivity of the 9-mer (SEQ ID NO: 2).

Example 2 Therapeutic Effects of 9-Mer on Desiccation Induced-Dry Eye Syndrome

Murine dry eye model established according to procedures set forth in "Materials and Methods" section was used in this example to evaluate the therapeutic efficacy of 9-mer (SEQ ID NO: 2) and its analogues.

Briefly, mice were housed at desiccating condition for 14 days to induce dry eye syndrome, which was evidence by corneal ulcer with fluorescein stain, a typical sign of dry eye, then treatment was applied at indicated time and dosage. Results are illustrated in FIG. 3.

Figure 3:
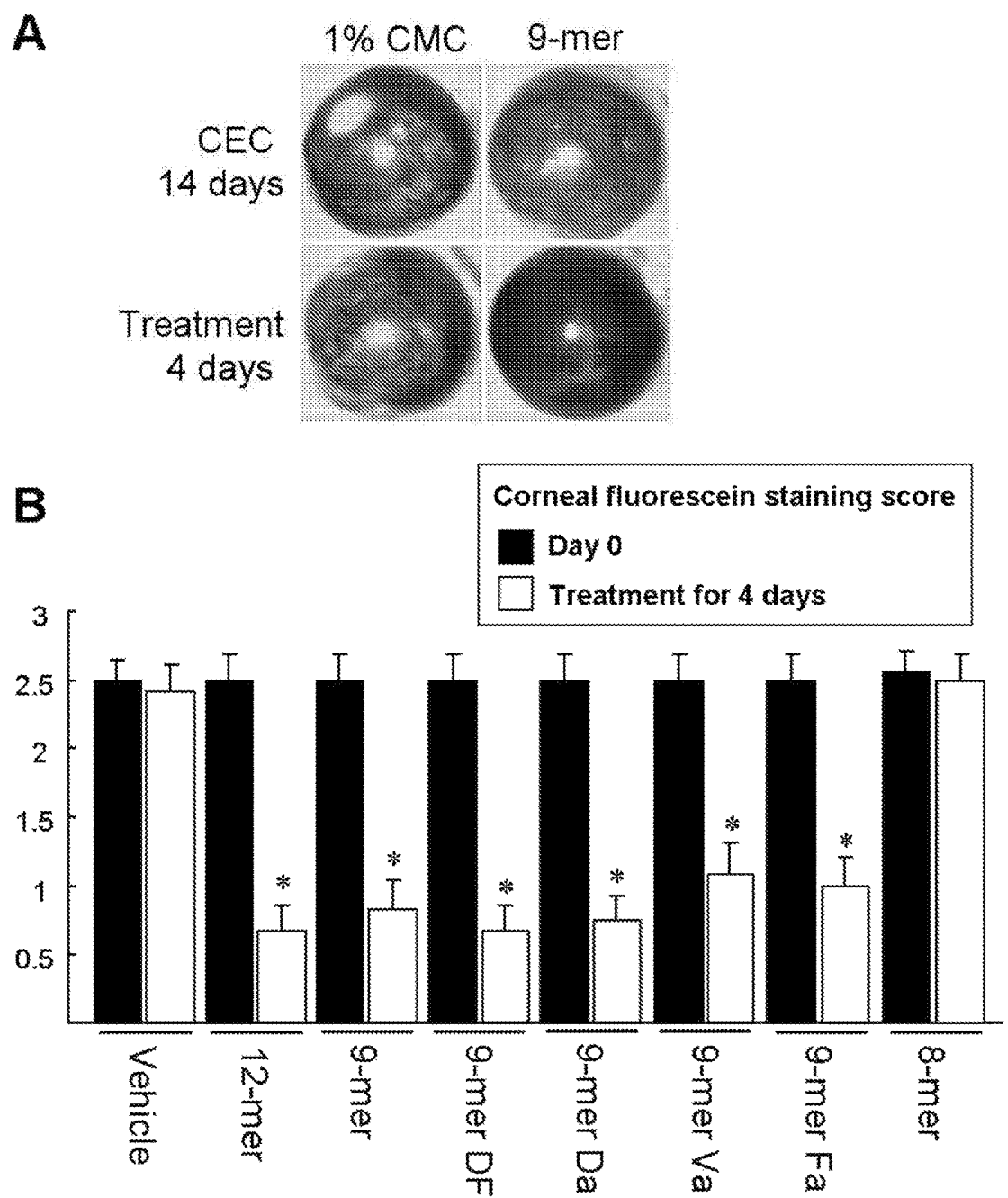
FIG. 3 illustrates the effects of 9-mer peptide (SEQ ID NO:2) on desiccation induced corneal surface injury determined by fluorescein staining in accordance with one embodiment of the present disclosure, A. Imagines of corneal fluorescein staining for estimating corneal damage; B. Averaged corneal fluorescein staining scores for indicating corneal damage, in which *$P<0.0002$ versus day 0.
Figure 4:
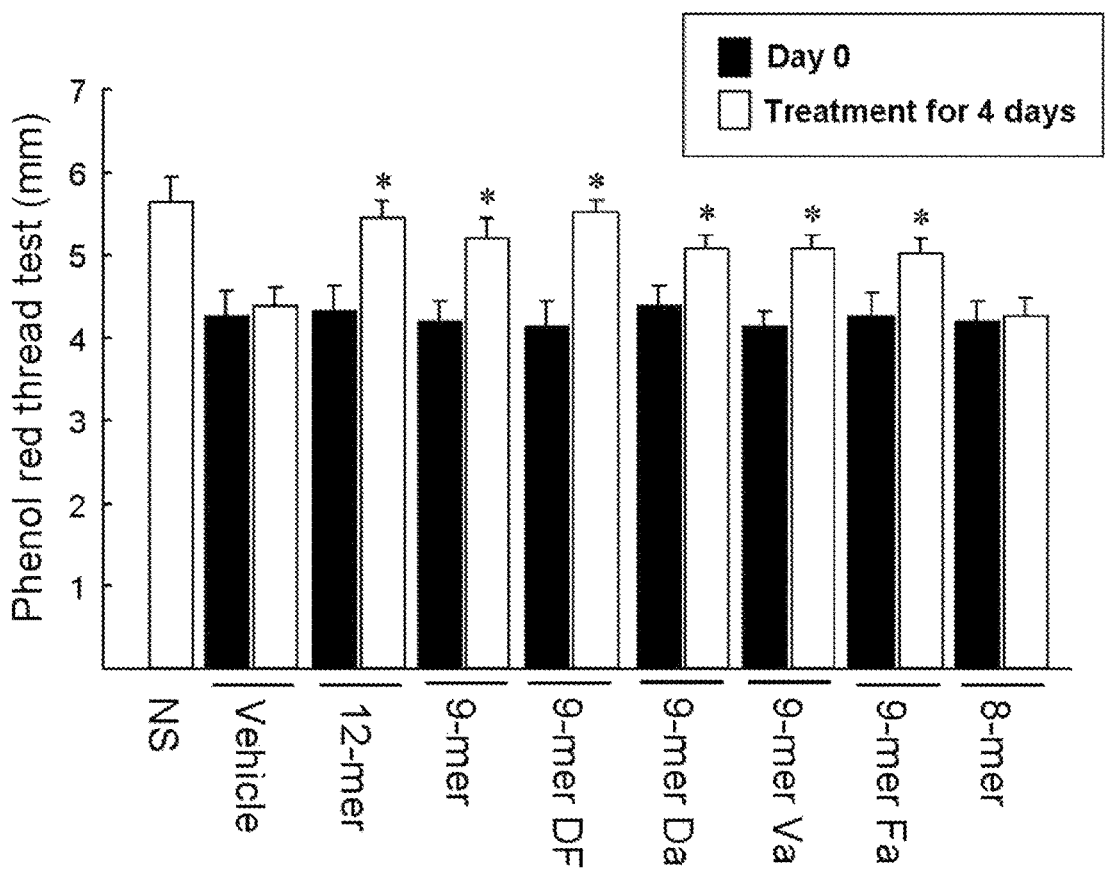
FIG. 4 illustrates the effects of 9-mer peptide (SEQ ID NO:2) on tear production determined by phenol red thread test in accordance with one embodiment of the present disclosure.

Photographs of eye balls treated with the control eye drop or eye drop containing 9-mer peptide (SEQ ID NO: 2) were provided in panel A of FIG. 3. The corneal fluorescein stain reduced significantly for mice receiving 9-mer (SEQ ID NO: 2) treatment for 4 days, which was an indication that 9-mer (SEQ ID NO: 2) possessed therapeutic function on dry eye. Similarly, dry eye treated with 12-mer (SEQ ID NO: 12), 9-mer (SEQ ID NO: 2), 9-mer DF (SEQ ID NO: 2), or 9-mer alanine analogues (9-mer Da (SEQ ID NO:3), 9-mer Va (SEQ ID NO: 7), or 9-mer Fa (SEQ ID NO: 11)) for 4 days, all displayed about 3-fold reduction in mean corneal fluorescein staining score, as compared with those of the vehicle treated control mice (FIG. 3, panel B). Further, the control 8-mer peptide (SEQ ID NO: 13), had no such effect. In addition, the tear volume was significantly increased in the eyes that were treated with 12-mer (SEQ ID NO: 12), 9-mer (SEQ ID NO: 2), 9-mer DF (SEQ ID NO: 2) and 9-mer alanine analogues (9-mer Da (SEQ ID NO:3), 9-mer Va (SEQ ID NO:7), and 9-mer Fa (SEQ ID NO:11)) for 4 days ($P<0.01$ versus vehicle treatment) (FIG. 4).

Example 3 Therapeutic Effects of 9-Mer on Human Multiple Myeloma Cells

In this example, the cytotoxic effects of 9-mer (SEQ ID NO:2) on the growth of human myeloma cells, including RPMI8226 cells and U266 cells, were investigated. Results are illustrated in FIGS. 5 and 6.

Figure 5:
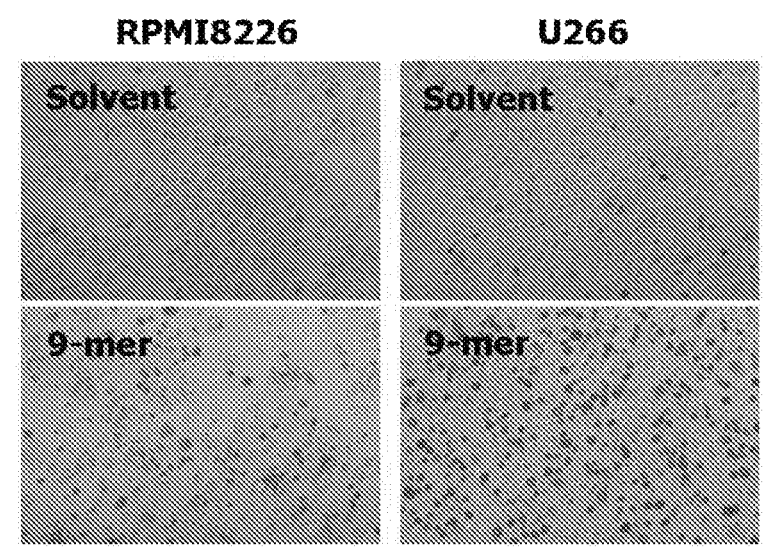
FIG. 5 illustrates the effects of 9-mer peptide (SEQ ID NO:2) on human multiple myeloma cells in accordance with one embodiment of the present disclosure, A. phase-contrast photographs of RPMI8226 and U266 cells stained by Trypan Blue; B. bar graph depicting the quantified result of panel A. Data were presented as mean±S.D. of three independent experiments.*$P<0.005$ versus solvent-treated cells.
Figure 5:
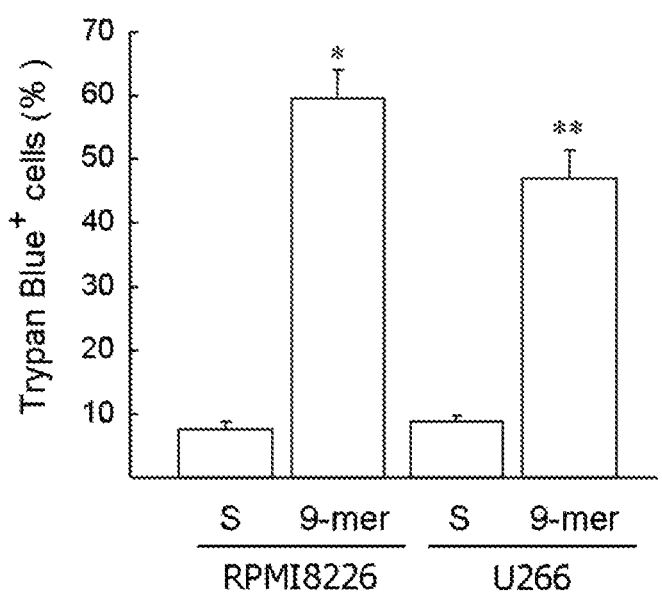
Figure 6:
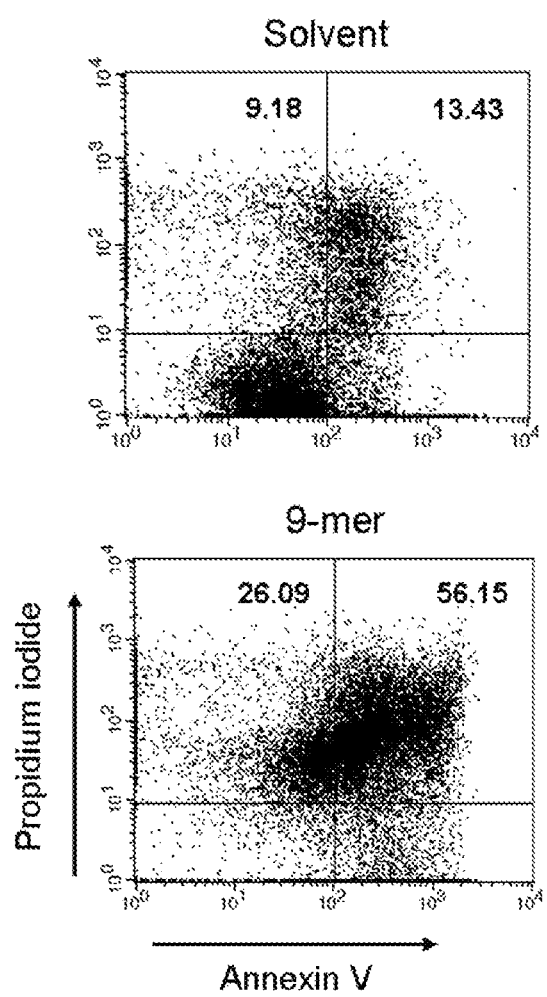
FIG. 6 illustrates the 9-mer peptide (SEQ ID NO:2) induced apoptosis on RPMI8226 cells in accordance with one embodiment of the present disclosure, A. Representative Annexin V versus Propidium iodide contour plots from 3 independent assays. B. Bar graph depicting the quantified result of panel A, in which data presented are the mean values for the percentage of apoptotic cells±S.D. *$P<0.002$ versus solvent-treated cells.
Figure 6:
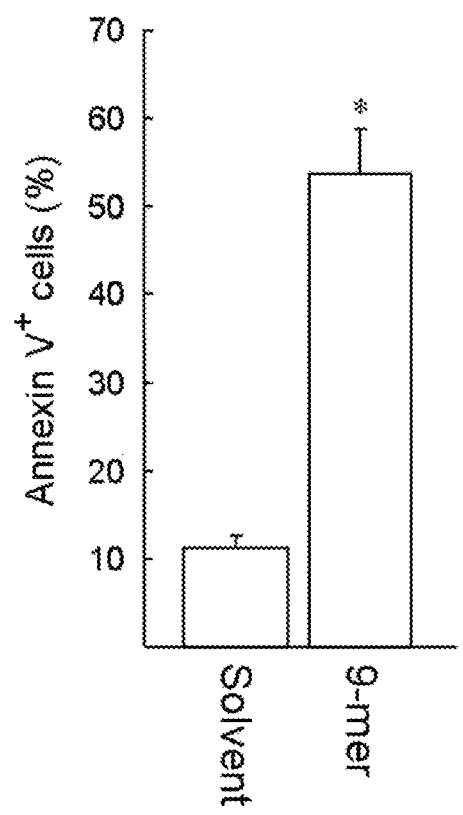

The cytotoxic effects of 9-mer (SEQ ID NO:2) on the growth of human multiple myeloma cells were determined by trypan blue assay, and the results indicated that as compared to 9-mer solvent (DMSO) treatment, 9-mer (SEQ ID NO:2) significantly decreased cell viability of RPMI8226 cells (7.5±1.3 vs 59.7±4.5) and U266 cells (8.7±1.1 vs 47.0±4.6), respectively (FIG. 5). The inhibitory effects of 9-mer (SEQ ID NO:2) was achieved by the induction of apoptosis in these cancer cells, as determined by annexin-V staining. Upon 9-mer (SEQ ID NO:2) treatment for 24 hr, approximately 54% of the myeloma cells exhibited apoptotic phosphatidylserine exposure, as compared to less than 15% of the cells appeared to be apoptotic in the control untreated cells (FIG. 6).

Example 4 Therapeutic Effects of 9-Mer on IMQ-Induced Psoriasis Vulgaris-Like Skin Inflammation Murine psoriasis vulgaris-like skin inflammation model established according to procedures set forth in "Materials and Methods" section was used in this example to evaluate the therapeutic efficacy of 9-mer (SEQ ID NO: 2) and its analogues.

Figure 7:
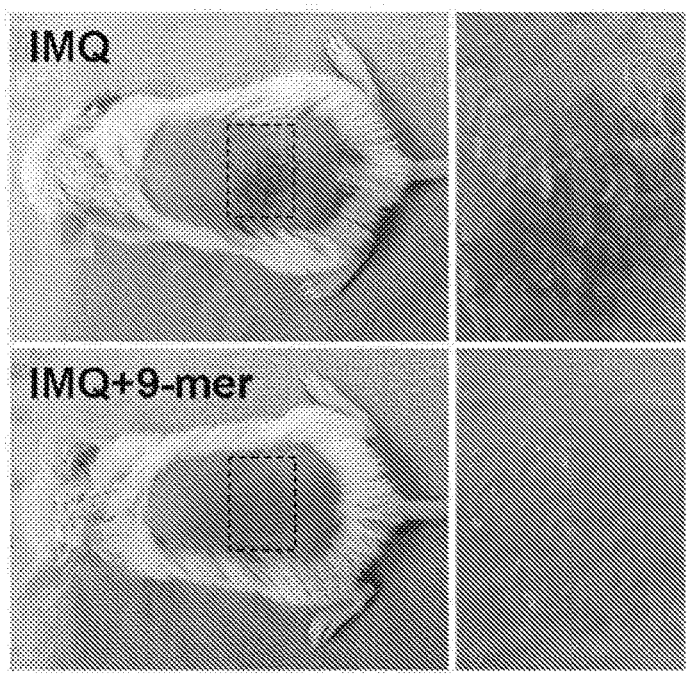
FIG. 7 are photographs of mice illustrating the effects of 9-mer peptide (SEQ ID NO:2) on IMQ-induced psoriasis vulgaris-like skin inflammation and desquamation formation in accordance with one embodiment of the present disclosure; A. Phenotypical presentation of mouse back skin after 6 days of treatment. Insert: back skin is visible at high-powered light-field camera. B. At the day 6, the ear thickness of the right ear was measured in duplicate using a micrometer. Average ear thickness (mm) was used to indicate the IMQ-induced skin inflammation. #$P<0.0001$ versus untreated normal mice. *$P<0.0001$ versus IMQ/vehicle-treated mice.
Figure 7:
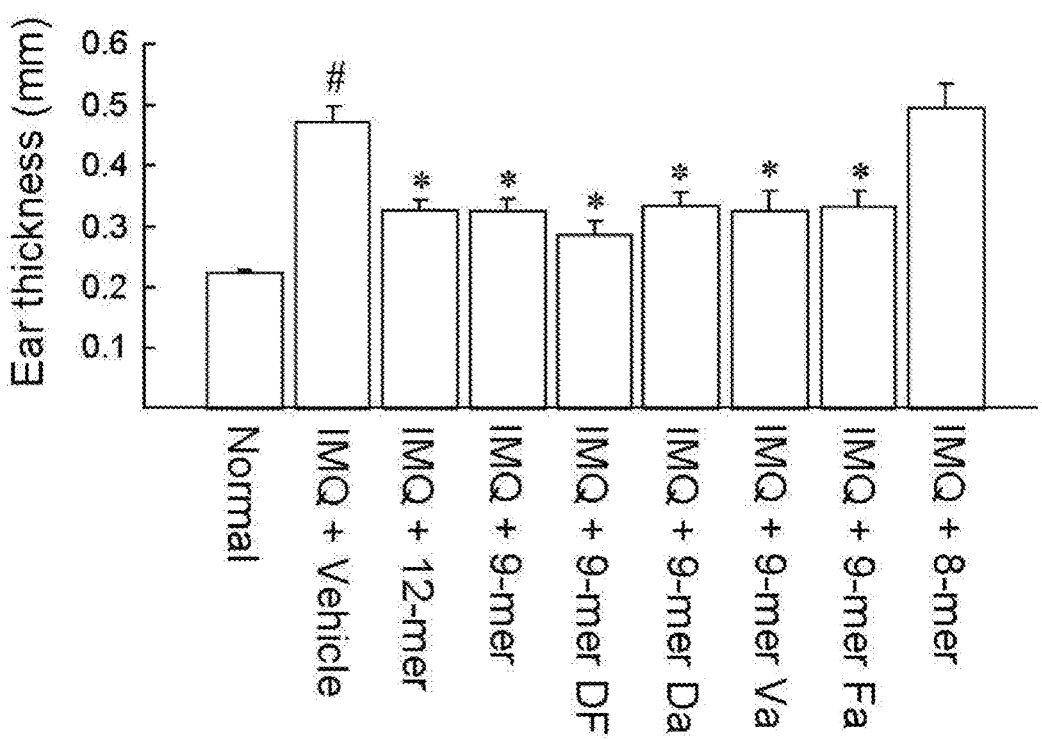

Briefly, BALB/c mice were given a daily topical IMQ treatment with or without the presence of 9-mer (SEQ ID NO:2) and/or its analogues (e.g., 12-mer (SEQ ID NO:12), 9-mer DF (SEQ ID NO:2), 9-mer Da (SEQ ID NO:3), 9-mer Va (SEQ ID NO:7), or 9-mer Fa (SEQ ID NO:11)) on the shaved back and the right ear for six consecutive days. During this time, the mice treated with IMQ alone developed psoriasis vulgaris-like skin inflammation and desquamation formation; whereas mice received topical application of IMQ and the 9-mer (SEQ ID NO:2) (25 μM), exhibited reduced level of dosal skin inflammation and desquamation (FIG. 7).

Figure 8:
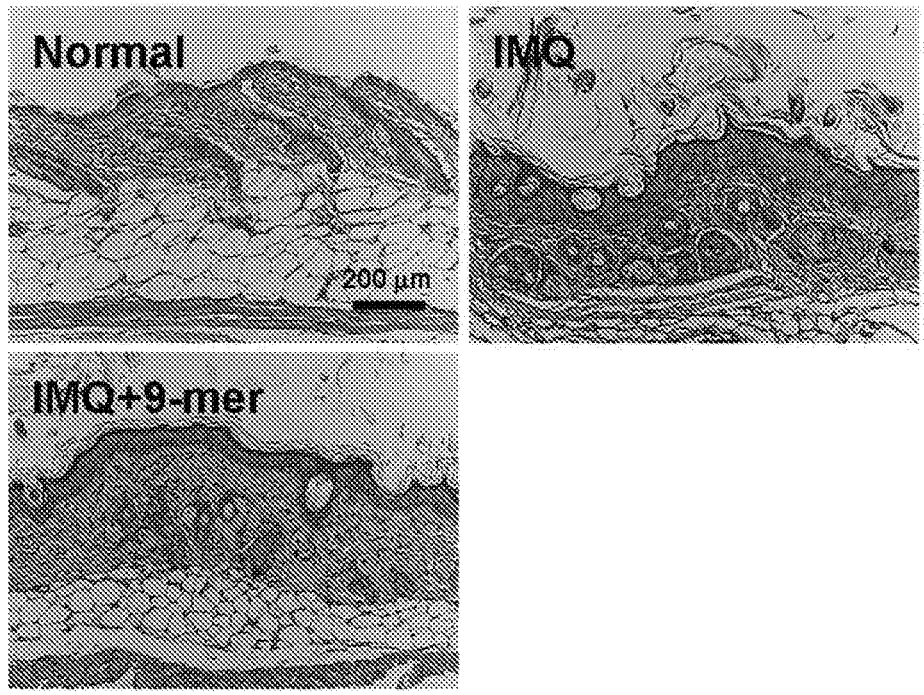
FIG. 8 illustrates the effects of 9-mer peptide (SEQ ID NO:2) on IMO-induced keratiocyte proliferation in accordance with one embodiment of the present disclosure; A. photographs of H&E staining of back skin sections of IMQ-treated mice with or without the presence of the 9-mer peptide. B. Bar graph illustrating the effects of 9-mer peptide (SEQ ID NO:2) or its analogues on the quantified epidermal thickness (μm) of skin sections obtained from IMQ-treated mice, in which *$P<0.0005$ versus IMQ control.
Figure 8:
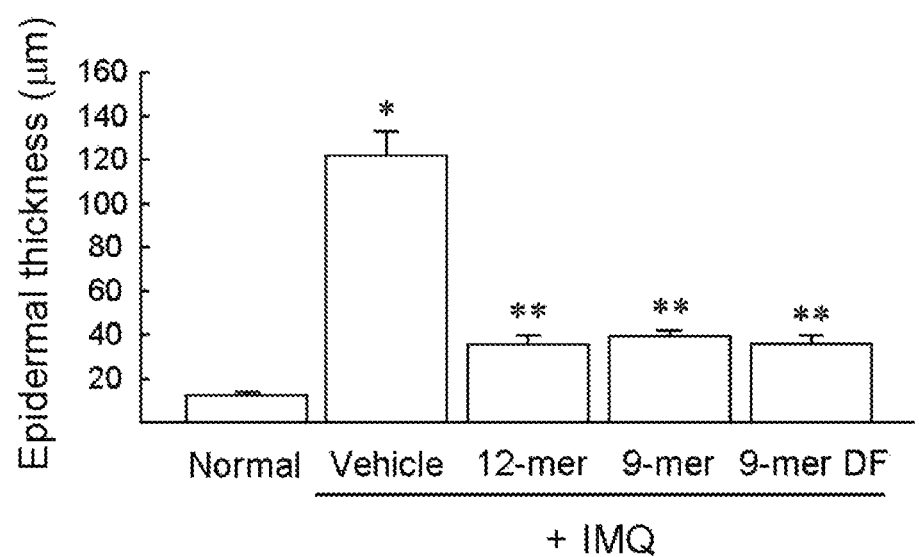

Microscopic examination of the skin sections of IMQ-treated mice revealed characteristic changes of psoriasis vulgaris lesions, such as acanthosis (thickening of the epidermis), desquamation and dermal infiltrate (H&E staining; FIG. 8, panel A). By contrast, skin sections that received 9-mer (SEQ ID NO:2) treatment exhibited decrease in acanthosis and less desquamation, as compared with that of the IMQ-treated skin sections. Similarly, if mice having psoriasis vulgaris-like skin inflammation received treatment of 12-mer (SEQ ID NO:12), 9-mer (SEQ ID NO:2), 9-mer DF (SEQ ID NO:2) peptide exhibited significant reduction in acanthosis, as compared with that of IMQ control (35.3±4.1, 39.2±2.7 and 35.7±4.2 versus 122±10.5; FIG. 8, panel B).

Figure 9:
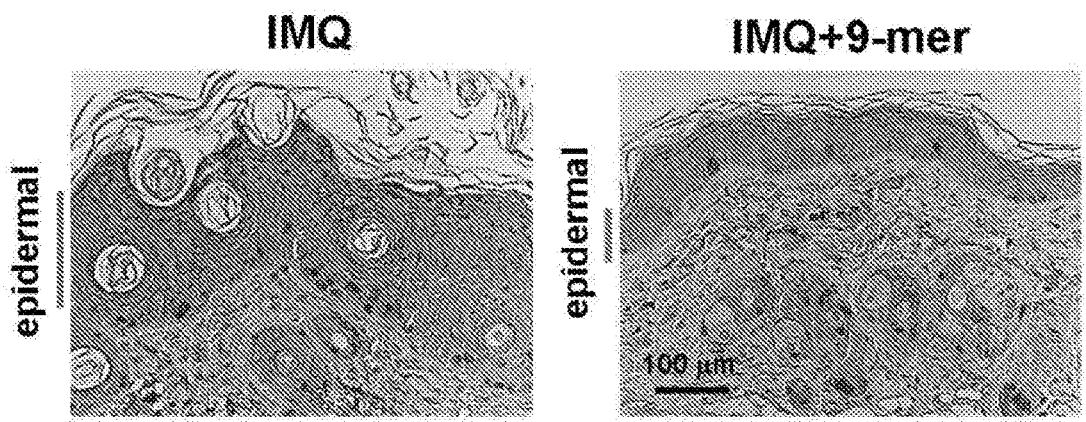
FIG. 9 illustrates the effects of 9-mer peptide (SEQ ID NO:2) and its analogues on IMO-induced keratiocyte proliferation determined by the numbers of BrdU-positive cells in the epidermis in accordance with one embodiment of the present disclosure, A. Histological analysis of cell replication at day 6 after IMQ treatment. B. Quantified results of BrdU-positive cells in the epidermis. The labeling index (%) was calculated as the number of labeled cells per HPF (200× high-power field). Data are representative of 10-16 HPF in each group, in which *$P<0.0001$ versus IMQ control.
Figure 9:
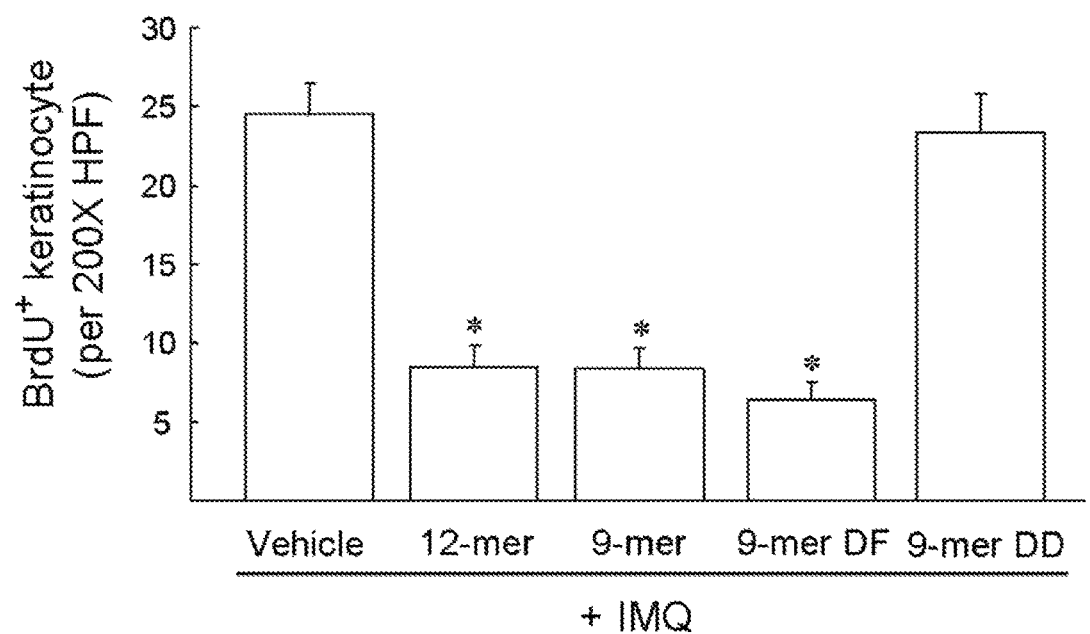

Hyperproliferation of keratinocytes on any of these skin sections was also monitored by BrdU incorporation. In IMQ-treated mice, as depicted in FIG. 9, panel A, BrdU was incorporated into DNA within keratinocytes (brown color) that are located throughout the various layers of the epidermis, reflecting dysregulated proliferation. In contrast, positive BrdU cells were found to restrict to the basal layer of the epidermis in IMQ+9-mer-treated mice. Similarly, significant reduction in the hyperproliferation of keratinocytes was found in mice receiving 12-mer (SEQ ID NO:12), 9-mer (SEQ ID NO:2), or 9-mer DF (SEQ ID NO:2) treatment, as compared with that of IMQ/9-mer DD (SEQ ID NO:2) (8.5±1.4, 8.3±1.4 and 6.3±1.2 versus 24.5±2.0 and 23.3±2.5; FIG. 9, panel B).

Taken together, the results presented in the afore-mentioned working examples confirm the short synthetic peptide of the present disclosure may be used for the treatment and/or prophylaxis of diseases or conditions related to, dry eye syndrome, psoriasis vulgaris or multiple myeloma.

It will be understood that the above description of embodiments is given by way of example only and that various modifications may be made by those with ordinary skill in the art. The above specification, examples and data provide a complete description of the structure and use of exemplary embodiments of the invention. Although various embodiments of the invention have been described above with a certain degree of particularity, or with reference to one or more individual embodiments, those with ordinary skill in the art could make numerous alterations to the disclosed embodiments without departing from the spirit or scope of this invention.

What is claimed is:

1. A synthetic peptide consisting of the amino acid sequence of SEQ ID NO: 11.

2. A pharmaceutical composition comprising an effective amount of the synthetic peptide of claim 1, and a pharmaceutically acceptable carrier.

3. The pharmaceutical composition of claim 2, wherein the pharmaceutical composition is in a form of a liquid, a gel, a cream, or an ointment.

4. A method of treating a subject suffering from dry eye syndrome, psoriasis vulgaris or multiple myeloma comprising administering to the subject an effective amount of a synthetic peptide consisting of the amino acid sequence of SEQ ID NO: 11.

5. The method of claim 4, wherein the synthetic peptide is administered in an amount of 0.01-100 mg/Kg.

6. The method of claim 4, wherein the subject is a human.

* * * * *